(12) United States Patent
Faurissoux et al.

(10) Patent No.: US 12,072,272 B2
(45) Date of Patent: Aug. 27, 2024

(54) METHOD FOR DETERMINING A RELATION BETWEEN AN INITIAL SATURATION AND A RESIDUAL SATURATION IN A FIRST FLUID IN A POROUS SAMPLE AND RELATED ASSEMBLY

(71) Applicant: TOTAL SA, Courbevoie (FR)

(72) Inventors: Pierre Faurissoux, Mazerolles (FR); Benjamin Nicot, Pau (FR); Bruno Lalanne, Morlaas (FR); Moeata Lutui-Tefuka, Pau (FR)

(73) Assignee: TOTALENERGIES ONETECH, Courbevoie (FR)

( * ) Notice: Subject to any disclaimer, the term of this patent is extended or adjusted under 35 U.S.C. 154(b) by 358 days.

(21) Appl. No.: 16/391,563

(22) Filed: Apr. 23, 2019

(65) Prior Publication Data

US 2019/0331578 A1 Oct. 31, 2019

(30) Foreign Application Priority Data

Apr. 25, 2018 (EP) .................................. 18305514

(51) Int. Cl.
*G01N 13/00* (2006.01)
*G01N 33/24* (2006.01)

(52) U.S. Cl.
CPC ........... *G01N 13/00* (2013.01); *G01N 33/241* (2013.01)

(58) Field of Classification Search
CPC .............................. G01N 13/00; G01N 33/241
USPC ............................................................. 73/37
See application file for complete search history.

(56) References Cited

U.S. PATENT DOCUMENTS

| | | | |
|---|---|---|---|
| 4,868,500 | A | 9/1989 | Baldwin et al. |
| 2013/0125630 | A1 | 5/2013 | Collins et al. |
| 2014/0055134 | A1 | 2/2014 | Fordham et al. |
| 2017/0023540 | A1 | 1/2017 | Bona |

FOREIGN PATENT DOCUMENTS

| | | |
|---|---|---|
| CN | 107831186 A | 3/2018 |
| EP | 1655617 B1 | 5/2006 |
| EP | 2006702 A2 | 12/2008 |

(Continued)

OTHER PUBLICATIONS

Bona, N., et al. "Trapped Gas Saturation Mesaurements: New Perspectives" Society of Petroleum Engineers, SPE-170765-MS, pp. 1-18 (Oct. 2014).

(Continued)

*Primary Examiner* — Alexander A Mercado
*Assistant Examiner* — Rodney T Frank
(74) *Attorney, Agent, or Firm* — TROUTMAN PEPPER HAMILTON SANDERS LLP

(57) ABSTRACT

A method for determining a relation between an initial saturation and a residual saturation in a first fluid in a porous sample, comprising the following steps saturating a porous sample with a second fluid; measuring a local volume of the second fluid in the porous sample; establishing a steady state profile of a saturation in the first fluid in the porous sample; generating a rise of a capillary ascension flow of the second fluid through the porous sample; during the capillary ascension flow, simultaneously measuring a local volume of the second fluid; and determining the relation between the initial saturation and the residual saturation based on the measured local volume.

13 Claims, 6 Drawing Sheets

(56) References Cited

FOREIGN PATENT DOCUMENTS

EP 3074762 A1 10/2016
WO 2012123863 A2 9/2012

OTHER PUBLICATIONS

Chen, Q., et al. "A magnetic resonance study of pore folling processes during spontaneous imbibition in Berea sandstone" Journal of Chemical Physics, 119(18) 9609-9616 (2003).
European Search Report issued in European Patent Application No. 18305514.4 dated Oct. 19, 2018.

METHOD FOR DETERMINING A RELATION BETWEEN AN INITIAL SATURATION AND A RESIDUAL SATURATION IN A FIRST FLUID IN A POROUS SAMPLE AND RELATED ASSEMBLY

CROSS REFERENCE TO RELATED APPLICATION

This application claims priority of European Patent Application No. 18305514.4 filed Apr. 25, 2018. The entire contents of which are hereby incorporated by reference.

FIELD OF THE INVENTION

The invention relates to a method for determining a relation between an initial saturation and a residual saturation in a first fluid in a porous sample.

BACKGROUND

During the production of an underground gas reservoir, the total initial amount of gas in the reservoir (called Gas In Place, GIP) is divided between a recoverable amount and a non-recoverable amount. Determining the recoverable and non-recoverable amounts of gas is crucial for planning the extraction phase and the most appropriate methods for the extraction.

Production of recoverable gas is frequently mainly done by depletion of gas driven by the rise of an underlying aquifer through the formation. With the pressure drop through depletion and the subsequent encroachment of the aquifer into the gas reservoir, water traps gas in the formation.

It is thus desirable to be able to determine the residual gas saturation (Sgr) in the rock formation, corresponding to non-recoverable gas after the rise of the aquifer, which strongly depends on the nature of the rock.

Several studies show a link between the initial gas saturation (Sgi) with the residual gas saturation in the rock formation, for a specific rock type. Sgi can be measured on rock samples extracted in the field, in order to predict Sgr through a relation obtained through modelling or experimentally.

The relation between Sgi and Sgr is generally modelled with a bilinear relation curve, with a first linear part for low values of Sgi and Sgr, and a plateau for higher values. However, these models only give an estimate value, only validated on homogenous rock types.

It is also possible to obtain an exact relation between Sgi and Sgr for a specific rock type through experimental work, but it requires a large number of experiments. This can thus prove to be a long and tedious process, depending on the permeability of the rock samples.

The existing experimental methods generally comprise providing a sample containing gas at an initial saturation and then flooding the sample through forced imbibition or capillary rise and measuring the residual gas saturation at steady state. This experiment must be repeated many times to provide an accurate Sgi/Sgr curve, and each experiment can take a long time with low-permeability rocks.

There is thus a need for a determination method of the relation between Sgi and Sgr that is both fast and accurate.

One aim of the invention is to provide a robust and efficient experimental method to provide a relation curve between Sgi and Sgr for a rock formation sample, able to provide accurate results in a reduced time, notably in a few days.

SUMMARY

To this aim, the subject-matter of the invention is a method of the afore-mentioned type, comprising the following steps:
providing a porous sample;
substantially saturating the porous sample with a second fluid;
measuring a local volume of the second fluid in a plurality of regions of the porous sample;
establishing a steady state profile of a saturation in the first fluid in the porous sample, by applying a mechanical load, creating in each region of the plurality of regions a different saturation in the first fluid;
measuring an initial local volume of the second fluid in each region of the porous sample;
generating a rise of a capillary ascension flow of the second fluid through the porous sample;
during the rise of the capillary ascension flow, simultaneously measuring, in each region of the plurality of regions, a local volume of the second fluid and/or of the first fluid, at successive instants, advantageously until the local volume is substantially steady;
determining the relation between the initial saturation in the first fluid and the residual saturation in the first fluid based on the local volume measured at successive instants in each region of the plurality of regions.

The method according to the invention may comprise one or more of the following feature, taken solely or according to any technically feasible combination:
the mechanical load is applied by centrifugating the porous sample around a rotation axis, a first end of the porous sample being oriented away from the rotation axis and a second end of the porous sample being oriented toward the rotation axis;
establishing the steady state profile in the porous sample comprises:
injecting the first fluid in the porous sample, forming an entry flow,
simultaneously collecting fluid from the porous sample, forming an exit flow; and
maintaining the mechanical load until a rate of the exit flow becomes substantially zero;
the local volume of the first fluid and/or of the second fluid, in each region of the plurality of regions, is measured through nuclear magnetic resonance imaging, or X-Ray tomography.
generating a rise of a capillary ascension flow of the second fluid through the porous sample includes:
submerging a first end of the porous sample in the second fluid, the first end being oriented downward with respect to gravity, and a second end being oriented upward;
maintaining a constant level of the second fluid around the first end of the porous sample during a capillary ascension of the second fluid through the porous sample;
the constant level of the second fluid is maintained in a plane with a second fluid feeding assembly comprising an upper burette and a lower burette containing the second fluid, an upper surface of the second fluid in the lower burette extending in the plane and an outlet of the upper burette opening in the lower burette, in the plane or below the plane;

the method comprises monitoring the position of an upper surface of the second fluid in the upper burette;

during the rise of the capillary ascension flow, the simultaneously measuring, in each region of the plurality of regions, of the local volume of the second fluid and/or in the first fluid, at successive instants is carried out without moving the porous sample;

in each region of the plurality of regions, the initial saturation in the first fluid is determined as the saturation in the first fluid corresponding to the initial local volume, and the residual saturation is determined as the saturation in the first fluid corresponding to a crossing of the tangents to the curve on each side of a change of regime in the capillary ascension through the porous sample;

the first fluid is a gas and the second fluid is a liquid, preferably a water-based liquid;

the porous sample is a formation sample, in particular a rock sample;

the porous sample is substantially cylindrical and has a central axis, each region of the plurality of regions being a transversal slice delimited by two parallel planes perpendicular to the central axis;

the steps of establishing a steady state profile, generating a rise of a capillary ascension flow and measuring the local saturation are repeated with different values of the mechanical load during the step of establishing a steady state profile.

The invention further concerns a system for determining a relation between an initial saturation and a residual saturation in a first fluid in a porous sample, the system comprising:

a measuring apparatus, for measuring a local volume of a second fluid in each region of a plurality of regions of the porous sample;

a load applicating apparatus for establishing a steady state profile of a saturation in the first fluid in the porous sample, by applying a mechanical load, to create in each region of the plurality of regions a different saturation in the first fluid;

a capillary rise apparatus for forming a capillary ascension flow of the second fluid through the porous sample;

a calculator for determining the relation between the initial saturation and the residual saturation in the porous sample based on the measured local volumes in each region of the plurality of regions.

The system according to the invention may comprise the following feature:

the measuring apparatus is a nuclear magnetic resonance imager, comprising a measuring cavity adapted to receive the porous sample in contact with the capillary rise apparatus.

BRIEF DESCRIPTION OF THE DRAWINGS

The invention will be better understood upon reading the following description, which is given only as an example, and made in reference to the joined drawings, among which.

DETAILED DESCRIPTION

Figure 1:
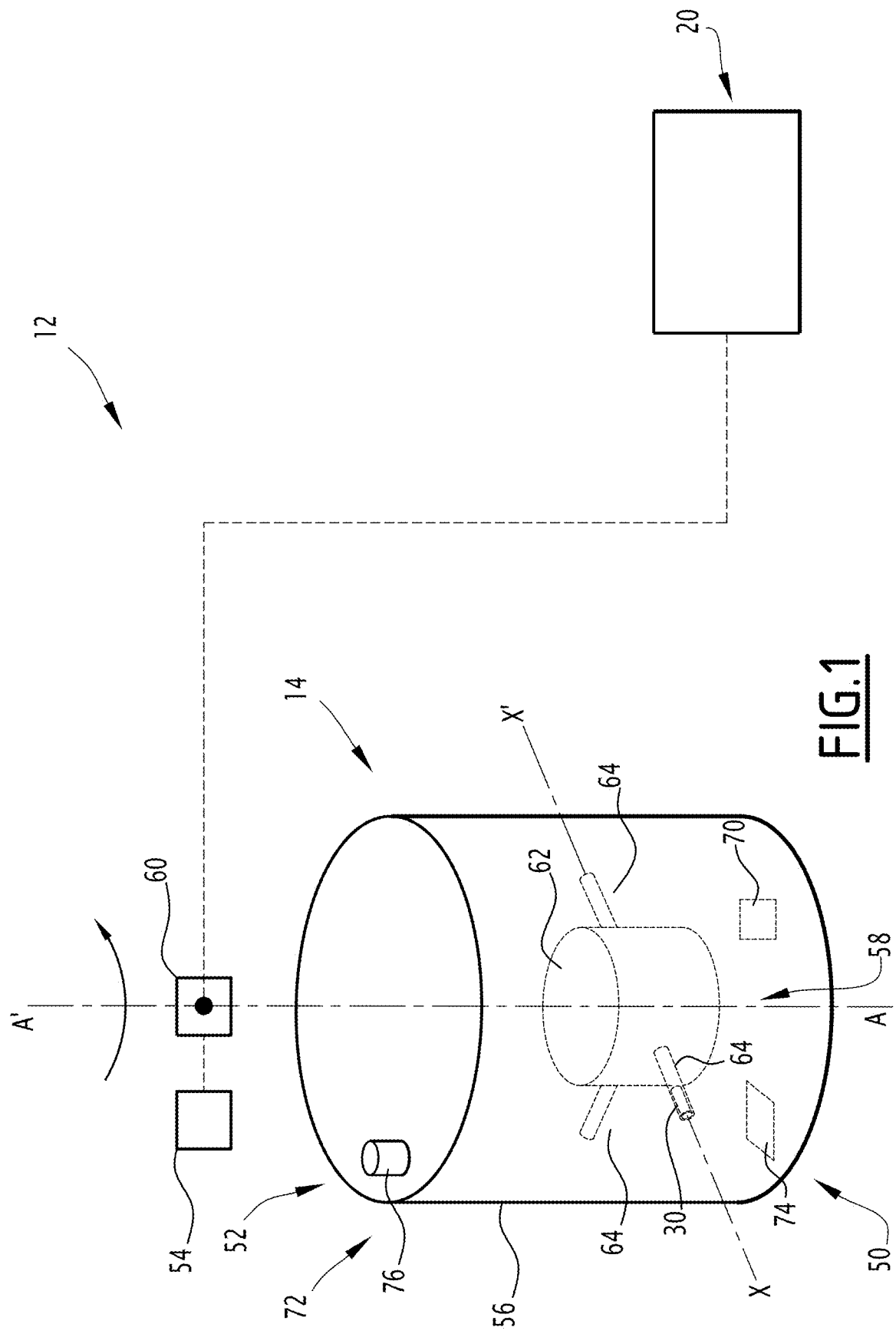
FIGS. 1 and 2 are schematic views of a apparatuses forming a system for carrying out a method according to the invention.
Figure 2:
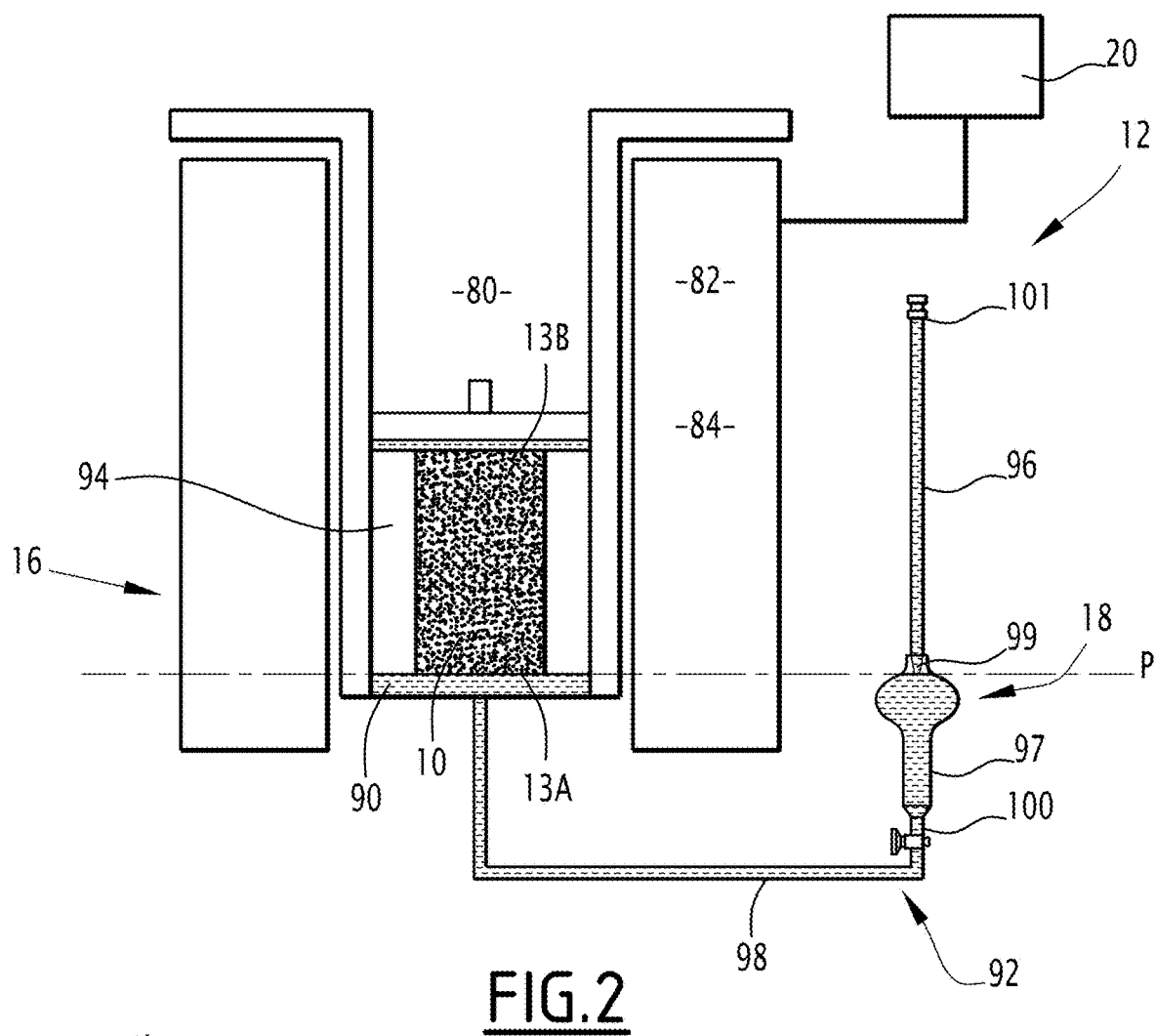

A method for determining a relation between an initial saturation Sgi and a residual saturation Sgr in a first fluid in a porous sample 10, represented on FIG. 2, is carried out in a system 12 schematically illustrated in FIGS. 1 and 2.

The porous sample 10 is for example a formation sample extracted from a sub-soil. The formation sample is in particular a rock sample extracted from a rock formation.

Typically, the porous sample 10 has for example a volume comprised between 8 cm$^3$ and 60 cm$^3$. It is advantageously cylindrical, with a circular cross-section, and has a central axis.

The porous sample 10 presents a first end 13A and a second end 13B along the central axis.

The diameter of the porous sample 10 is generally comprised between 23 mm and 40 mm. Its length is for example comprised between 20 mm and 50 mm.

In a variant, the porous sample 10 is a parallelepiped.

The porous sample 10 presents an internal porosity, constituting a free space delimited by a solid part of the porous sample. The porous sample 10 is able to receive at least one fluid in the internal porosity.

The first fluid is for example a gas, notably air, or a petroleum gas, or an oil-based fluid.

The second fluid is for example a water-based fluid, notably water or brine. The second fluid is notably substantially non miscible with the first fluid. The second fluid typically presents a higher density than the first fluid.

The saturation in the first fluid, respectively in the second fluid, in the porous sample 10, is a ratio of a pore volume occupied by the first fluid, respectively by the second fluid, in the internal porosity, divided by a total pore volume of the internal porosity.

The saturation in the first fluid or in the second fluid can be expressed locally, relative to a region of the porous sample 10, as a ratio of the pore volume in the region occupied by the first fluid, respectively by the second fluid, to the total pore volume in the region.

The system 12 comprises a loading apparatus 14, represented on FIG. 1, for establishing a steady state profile of the saturation in the first fluid in the porous sample 10 by applying a mechanical load to create in each region of a plurality of regions a different saturation in the first fluid.

The system 12 also comprises a measuring apparatus 16, represented on FIG. 2, for measuring a local volume of the second fluid in each region of the plurality of regions of the porous sample 10.

The system 12 further comprises a capillary rise apparatus 18, represented on FIG. 2, for generating a rise of a capillary ascension flow of the second fluid through the porous sample 10.

The system 12 further comprises a calculator 20 for receiving, storing and analyzing measurement results and determining the relation between the initial gas saturation Sgi and the residual gas saturation Sgr in the porous sample 10.

Figure 3:
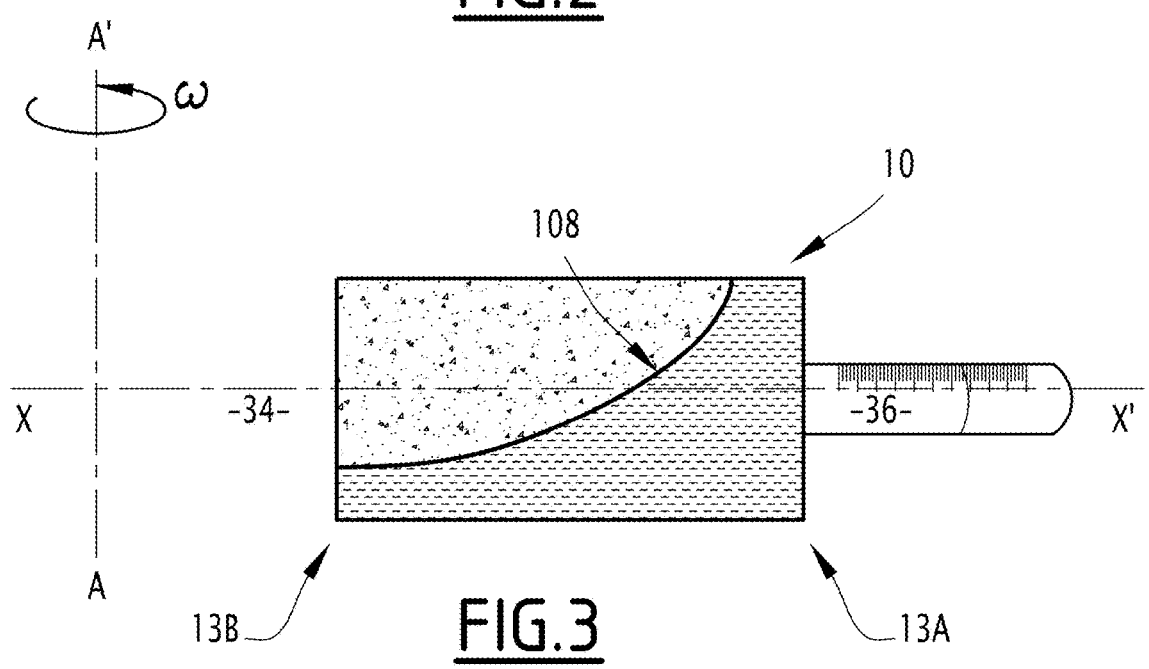
FIG. 3 is a schematic view of a porous sample, illustrating a steady state profile of a first fluid saturation in the sample.

In reference to FIGS. 1 and 3, the loading apparatus 14 comprises a cell 30 defining a volume for receiving the porous sample 10, an upstream chamber 34, for injection of the first fluid in the porous sample 10, and a downstream chamber 36 for receiving fluids collected when the mechanical load is applied to the porous sample 10.

The cell 30 is advantageously substantially cylindrical, and extends along a longitudinal axis X-X' coaxial with the central axis of the porous sample 10.

The cell 30 further defines an inlet for feeding the first fluid into the upstream chamber 34.

As shown in FIG. 1, the loading apparatus 14 here includes a centrifuge 50 to provide the mechanical load to the porous sample 10, a sensing system 52, and a control unit 54.

The centrifuge 50 comprises an enclosure 56, a rotor 58 rotatably mounted in the enclosure 50 around a rotation axis A-A', and a motor 60 able to drive the rotor 58 in rotation around axis A-A'.

The rotor 58 is contained in the enclosure 56. It is able to receive at least two cells 30, preferably at least three cells 30 containing each a porous sample 10.

In the example of FIG. 1, the rotor 58 comprises a central hub 62 and several radially protruding arms 64.

Each arm 64 receives a cell 30. The arms 64 are angularly distributed around the axis A-A'. The cell 30 is received with the longitudinal axis X-X' extending radially in reference to the rotation axis A-A'. The upstream chamber 34 is located relatively closer to the rotation axis A-A'. The downstream chamber 36 is located relatively away from the axis of rotation A-A'.

The porous sample 10 is thus arranged in the cell 30 with the first end 13A of the porous sample 10 oriented away from the rotation axis A-A' and the second end 13B of the porous sample 10 oriented toward the rotation axis A-A'.

The motor 60 of the centrifuge 50 is able to be actuated by the control unit 54 to rotate the rotor 58 and jointly the cell 30 containing the porous sample 10 at a speed of rotation w, preferably ranging from 500 rpm to 14000 rpm.

The mechanical load is therefore a centrifugal force applied on the porous sample 10 and the fluids contained in the porous sample 10.

The sensing unit 52 comprises a rotation speed sensor 70, able to detect the speed of rotation of the rotor 58, and a steady state detector 72.

The steady state detector 72 is able to monitor the rate of fluid production from the porous sample 10 during rotation of the cell 30 around the rotation axis A-A'.

In the example of FIG. 1, the steady state detector 72 advantageously comprises at least a stroboscope 74, and a camera 76 able to take images of the content of the downstream chamber 36 and/or of the upstream chamber 34 along time.

The control unit 54 is able to analyze the fluid production from the images taken with the camera 76 and to relate it to a rate of production of fluid in the downstream chamber 36 and/or in the upstream chamber 34 by image analysis.

The measuring apparatus 16 is adapted to measure the local volume of the second fluid in a region of the plurality of region of the porous sample 10.

The measuring apparatus 16 is for example a nuclear magnetic resonance imager, comprising a measuring cavity 80, and a field generator 82 and an antenna 84 arranged around the measuring cavity.

The measuring cavity 80 is adapted to receive the porous sample 10, alone and/or placed in the capillary rise apparatus 18. Notably, the measuring cavity 80 can be accessed with the capillary rise apparatus 18 from the outside during operation of the measuring apparatus 16, for example through an opening on top of or under the measuring apparatus 16.

The field generator 82 is adapted to generate a variating electromagnetic field in the cavity 80, with controlled intensity and spatial distribution.

The antenna 84 is adapted to measure a localized nuclear magnetic resonance signal in the measuring cavity 80 against time.

The regions are transversal slices of the porous sample 10 taken in succession longitudinally along the length of the porous sample 10. Each slice is delimited by two parallel transverse planes which are perpendicular to the central axis of the porous sample 10.

The length of each region, defined as the distance separating the planes delimiting the region, is for example comprised between 100 nm and 10 mm, and preferably between 500 nm and 5 mm. There are for example between 100 and 1000 regions in the porous sample 10, notably between 300 and 600.

Based on the nuclear magnetic resonance signal measured in each region, the calculator 20 is able to determine the local volume of first fluid and/or second fluid in each region in the porous sample 10.

Notably, the signal measured by the measuring apparatus 16 is directly proportional to a quantity of water molecules in the region, and thus directly linked to the volume of the second fluid in the region.

In a variant, the measurement apparatus 16 is an X-ray tomograph.

The capillary rise apparatus 18 is destined to form a capillary ascension flow of the second fluid through the porous sample 10. The capillary rise apparatus 18 comprises a reservoir 90, adapted to be arranged in the measuring cavity 80 and to receive the porous sample 10 and the second fluid.

The capillary rise apparatus 18 further comprises a feeding assembly 92, adapted to maintain a constant level of the second fluid in the reservoir 90 around the porous sample 10 during the capillary ascension.

The porous sample 10 is disposed in the reservoir 90 with the first end 13A of the porous sample 10 submerged in the second fluid and directed downward with respect to gravity. The second end 13B is directed upward with respect to gravity, and is outside the second fluid, so as to create a capillary ascension flow of the second fluid through the sample 10, from the first end 13A towards the second end 13B.

Advantageously, the sample 10 is placed in a sleeve 94 to prevent fluids from entering or exiting the porous sample through the lateral face of the sample 10. The sleeve 94 is in particular made in a material transparent to the electromagnetic fields generated by the field generator 82.

The feeding assembly 92 comprises for example an upper burette 96, a lower burette 97 and a feeding conduit 98.

The upper burette 96 is arranged on top of the lower burette 97, with an outlet 99 of the upper burette 96 being located in an inlet of the lower burette 97, allowing air to pass from outside of burettes 96 and 97 to the inside of burette 96 when the liquid level in burette 97 falls below plane P. An outlet 100 of the lower burette 97 is fluidically connected with the reservoir 90 through the feeding conduit 98. An inlet 101 of the upper burette 96 is closed in an air-tight manner, so as to prevent an air pressure in the upper burette 96 to equilibrate with the surrounding air.

The upper burette 96 and the lower burette 97 both contain the second fluid, with an upper surface of the second fluid defining a level in the lower burette 96 extending in the same plane P, perpendicular to the gravity, as the level maintained in the reservoir 90. The outlet 99 of the upper burette 96 opens in the same plane P as the levels in the lower burette 97 and in the reservoir 90, or below.

Thus, any lowering of the level of the second fluid in the reservoir 90, for example through imbibition in the porous sample 10, lowers the level in the lower burette 97, and creates a compensation flow of the second fluid from the upper burette 96, so as to maintain the level in the reservoir 90 at a constant height during the capillary ascension.

Advantageously, a detector (not shown) monitors the upper surface position in the upper burette 96 to relate it to the volume of fluid imbibed in the porous sample 10.

The calculator 20 advantageously comprises at least a processor and a least a memory containing software modules able to be executed by the processor. The memory contains at least a data recording module, for recording measurement data measured by the measurement apparatus 16, a data processing module, able to calculate saturations at each measured instant ion each region of the porous sample 10, based on the recorded measurement data, and a data analysis module able to calculate Sgi and Sgr values at each measured position and to plot a Sgr versus Sgi curve based on the calculated values.

A method for determining a relation between an initial saturation and a residual saturation in a first fluid in a porous sample 10, using the system 12, will now be described.

Initially, the porous sample 10 is provided, and saturated with a second fluid, in particular with a water-based fluid, notably water or brine.

Figure 4:
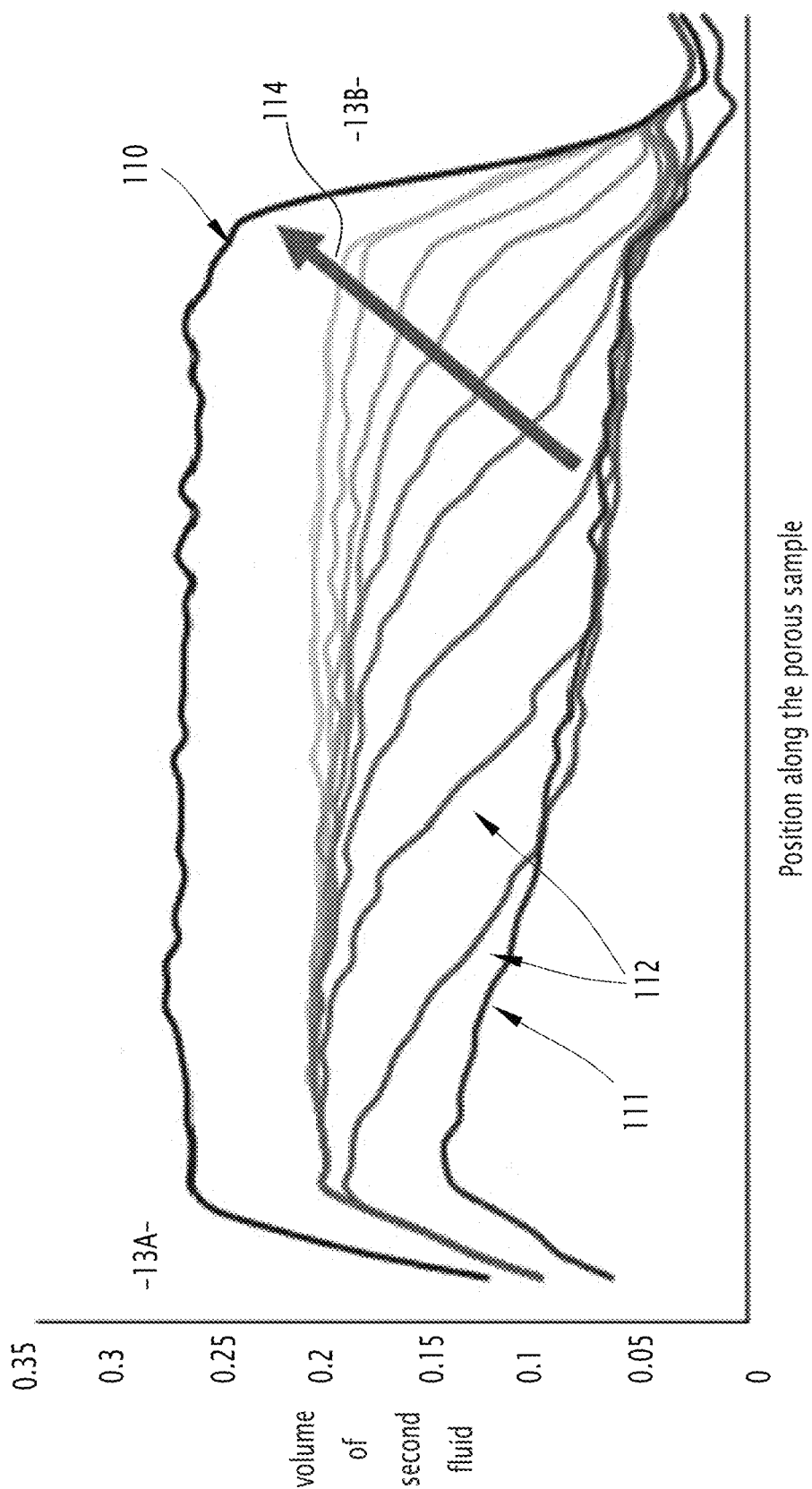
FIGS. 4 and 5 are plots profiles, respectively of a local volume of a second fluid and of a local saturation in the first fluid, during a capillary rise of the second fluid in the porous sample.

The porous sample 10 is then inserted in the measuring cavity 80 of the measuring apparatus 16, and a calibration profile is measured, represented by curve 110 on FIG. 4. The first end 13A is located on the left of the plot and the second end 13B on the right of the plot.

The calibration profile corresponds to the measured signal intensity in each region of the porous sample 10 for a saturation in the second fluid equal to one. As the signal corresponding to the solid part of the porous sample 10 is usually negligible, there is a linear relation between the measured signal intensity in each region and the local volume of the second fluid in the region.

Then, the porous sample 10 filled with the second fluid is inserted into the cell 30.

The cell 30 is introduced in the centrifuge 50. It is placed in an arm 64 of the rotor 58 with the axis X-X' of the porous sample 10 extending radially with regards to the axis of rotation A-A' of the rotor 58.

A first fluid is introduced in the upstream chamber 34 located closer to axis A-A'. The first fluid is for example an oil-based fluid, or a gas, notably a petroleum gas.

Then, the control unit 54 of the centrifuge 50 is activated to actuate the motor 60 and rotate the rotor 58 jointly with the porous sample 10 contained in the cell 30 around the rotation axis A-A'. A mechanical load applies on the porous sample 10 due to the centrifugal force applying on the porous sample 10.

The central axis of the porous sample 10 extends radially with regard to the rotation axis A-A'. The first end 13A of the porous sample 10 is oriented away from the rotation axis A-A' and the second end 13B of the porous sample 10 is oriented toward the rotation axis A-A'.

The first fluid contained in the upstream chamber 54 progressively penetrates into the porous sample 10 to generate a profile of saturation in the second fluid which is represented schematically with curve 108 in FIG. 3.

The first fluid injected in the porous sample 10 forms an entry flow through the second end 13B, and fluid, comprising a mixture of the first fluid and the second fluid, is extracted through the first end 13A, forming an exit flow.

The steady state detector 72 of the sensing unit 52 is activated to measure the rate of fluid extraction from the porous sample 10 collected in the downstream chamber 36.

In a time period comprised generally between one hour and several days, during which the mechanical load is maintained substantially constant (preferentially +/−5% of a set speed of rotation in case of centrifugation use), the first fluid content steady state profile establishes in the porous sample 10, when the rate of fluid extraction measured by the steady state detector 72 becomes zero.

In the steady state profile of saturation in the first fluid, each region of the porous sample 10 contains the first fluid with a different saturation, with the regions closer to the first end 13A having a lower saturation in the first fluid and the regions closer to the second end 13B having a higher saturation in the first fluid.

Figure 5:
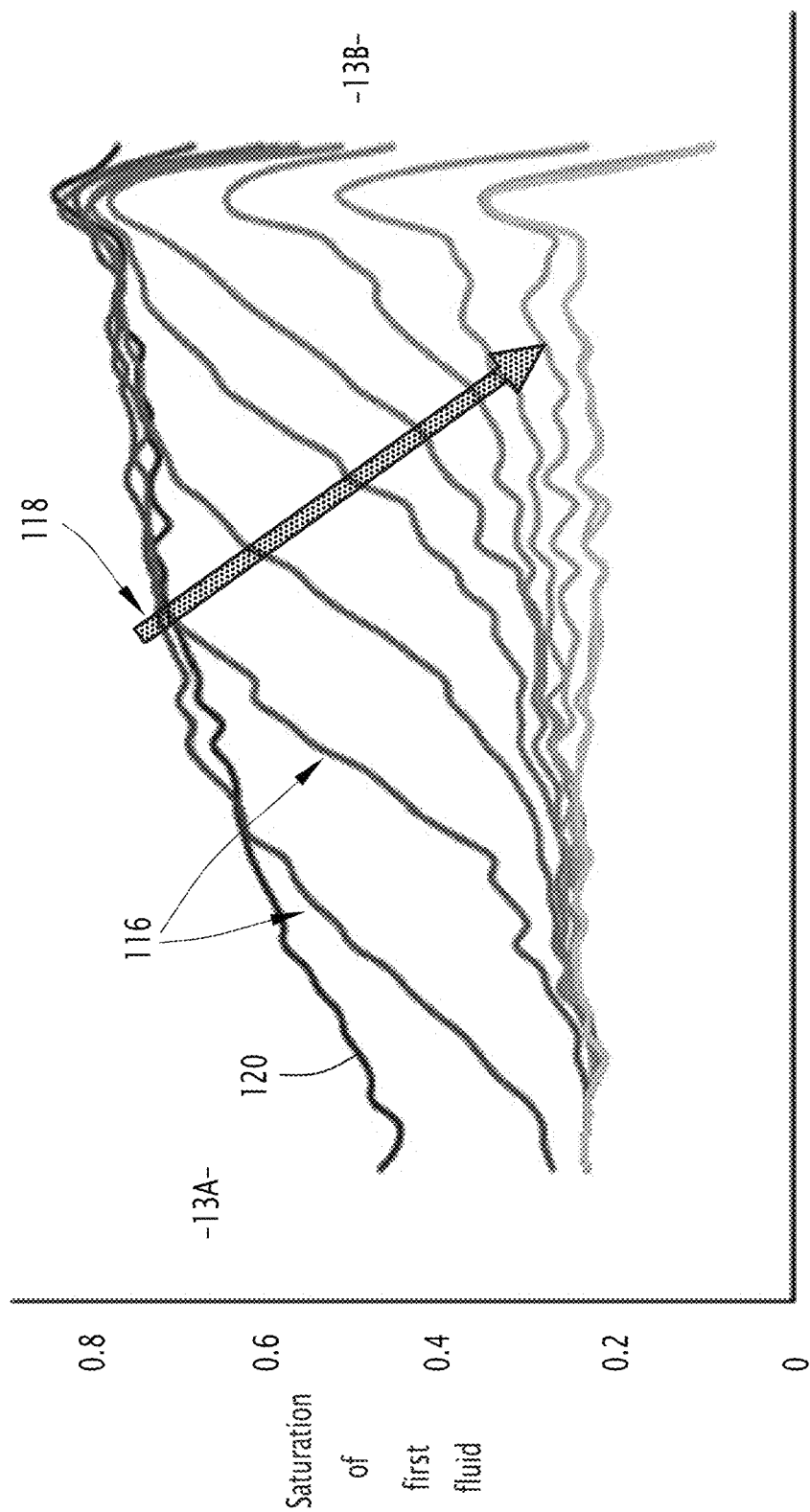

The porous sample 10 is transferred to the measuring apparatus 16 in order to measure an initial local volume profile 111 of second fluid in each region, represented on FIG. 4. The initial local volume profile 111 is then used to determine an initial profile 120 of the saturation in the first fluid, represented on FIG. 5. The initial profile 120 corresponds to the steady state profile established in the porous sample 10, and is used to determine the initial local saturation Sgi in the first fluid.

The porous sample 10 is then transferred to the measuring apparatus 16 receiving the reservoir 90. The porous sample 10 is placed in the reservoir 90, advantageously with the first end 13A submerged in the second fluid and oriented downward.

The upper part of the porous sample 10 protrudes upwardly out of the reservoir 90.

As the regions closer to the first end 13A have a higher saturation in the denser second fluid, this orientation reduces the risk of a gravity-induced fluid migration modifying the profile of saturation in the first fluid in the porous sample.

The capillary rise apparatus 18 generates a rise of a capillary ascension flow of the second fluid from the reservoir 90 through the sample, from the first end 13A toward the second end 13B.

The measurement apparatus 16 continuously measures the evolution of the local volume of the second fluid in each region of the porous sample 10 during the capillary ascension, in relation with the calibration profile. The measurement is done at successive instants, for example with a time period comprised between 5 min and 2 hours, until the local volume of the second fluid is substantially steady in each region of the porous sample 10.

An evolution of the local volume of the second fluid as a function of position and time is recorded in the calculator 20, and used to determine an evolution of the profile of the saturation in the second fluid in the porous sample 10, in reference to the calibration profile.

As plotted on FIG. 4, each curve 112 is a profile of the volume in the second fluid in the porous sample 10. The first end 13A is located on the left of the plot and the second end 13B on the right of the plot. The curves 112 representing the volume in the second fluid during the capillary ascension are arranged following the arrow 114, relative to the time, at successive instants in which the measurement was carried out.

The saturation in the first fluid in each region is obtained from the saturation in the second fluid as their sum is equal to one. The evolution of the saturation in the first fluid is plotted on FIG. 5, with each curve 116 being a profile of the saturation in the porous sample 10. The curves 116 representing the saturation in the first fluid during the capillary ascension are arranged following the arrow 118, relative to the time.

For each region of the porous sample 10, the initial saturation Sgi in the first fluid is taken as the saturation in the first fluid in the initial profile 120 obtained before the capillary ascension step.

Figure 6:
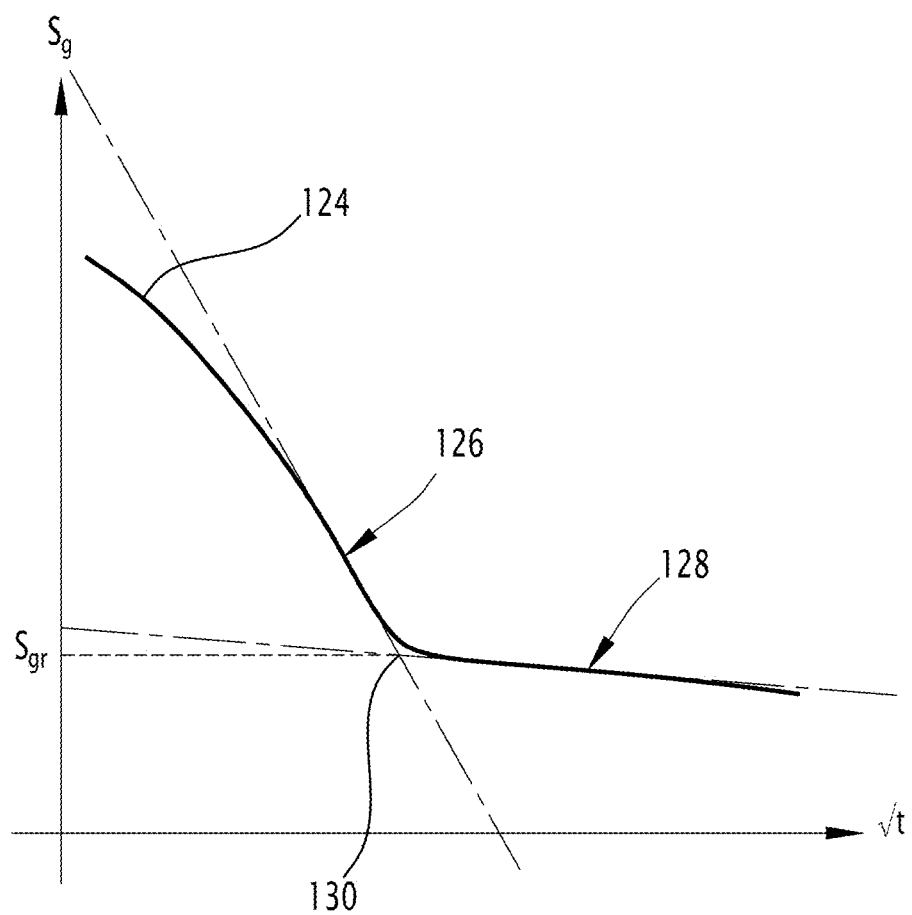
FIG. 6 is a plot of the evolution of a local saturation in the first fluid in the porous sample, against the square root of time, during the capillary rise.

In order to determine the residual saturation Sgr in the first fluid, for each region in the porous sample, the data analysis module of the calculator 20 determines a curve 124 of the evolution of the saturation in the first fluid plotted against the square root of time, as shown in FIG. 6.

The curve 124 presents a sharp drop 126 followed by a plateau 128, corresponding respectively to a capillary ascension regime and to a diffusion driven regime. The tangents to the curve are determined close to the transition, and the value of the saturation in first fluid corresponding to their crossing 130 is taken as the residual saturation Sgr in the first fluid in the region.

Figure 7:
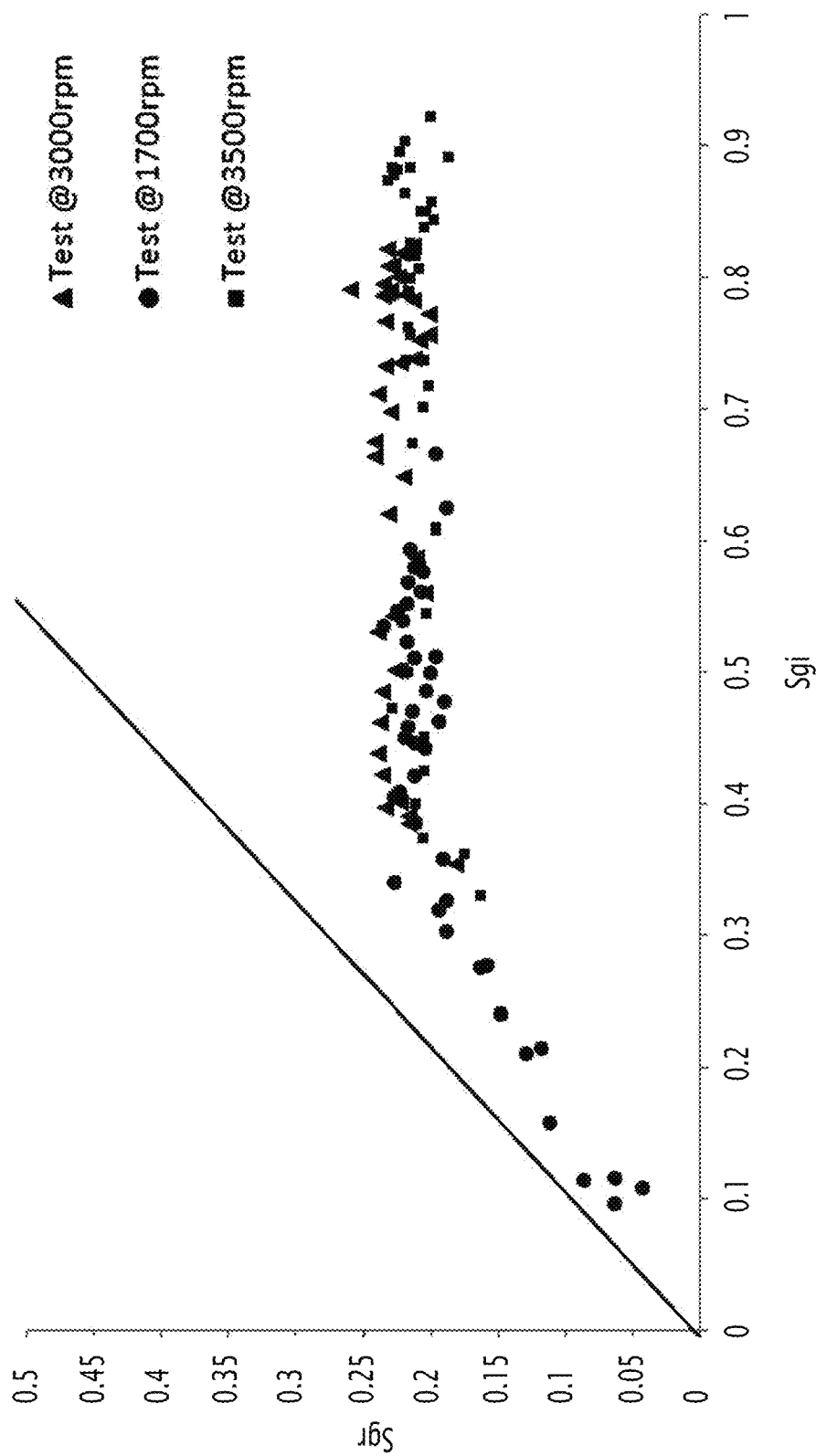
FIG. 7 is a plot of a relation between an initial saturation and a residual saturation in the first fluid in the porous sample.

Then, the data analysis module of the calculator determines the Sgi/Sgr curve, plotted on FIG. 7. Each region of the porous sample 10 in which a measurement was made at different instants during imbibition of the sample corresponds to a point in the Sgi/Sgr curve, plotted on FIG. 7.

In a variant, in order to tackle a larger number of values of initial saturation Sgi in the first fluid in the sample 30, the steps of establishing a steady state profile, forming a capillary ascension flow and measuring the local volume described above are repeated with different values of the mechanical load, with the same porous sample 10.

For example, the rotation speed w of the centrifuge 50 is modified, in order to reach a different steady-state profile and thus a different initial profile 120 of saturation in the first fluid.

This is represented on FIG. 7, the values plotted have been obtained through three successive experiments, with three different values of the rotation speed w, respectively plotted with triangles, circles and squares.

The method according to the invention allows a significant number of points of the Sgi/Sgr curve to be measured simultaneously in the same porous sample 10. With a typical number of regions in the porous sample around 400, the Sgi/Sgr relation curve is thus populated much faster than with previously existing experimental methods.

This is crucial in the case of samples extracted from a production field, as the results of the measurements can be provided to the operations in a few weeks, as opposed to several months in using state of the art techniques.

The results can then be integrated in the field study, after the drilling of a well has been made. The calculation of potential reservoir capabilities is made at an early stage, which is extremely favorable in terms of further operations in the field.

The method according to the invention is easy to carry out, and does not require a large amount of man force, and/or numerous porous samples 10.

Additionally, the experimental method circumvents the problems that arise with long saturation times with a fluid-gas mix, including dissolution and diffusion, which can alter the results significantly.

The invention claimed is:

1. A method for determining a relation curve between an initial saturation and a residual saturation in a first fluid in a porous sample, the method comprising:
   providing a porous sample;
   substantially saturating the porous sample with a second fluid;
   measuring a local volume of the second fluid in a plurality of regions of the porous sample;
   introducing a first fluid in the porous sample and applying a mechanical load to establish a steady state profile of a saturation in the first fluid in the porous sample and to create in each region of the plurality of regions, a different saturation in the first fluid;
   measuring an initial local volume of the second fluid in each region of the porous sample, and determining a measured initial saturation in the first fluid in each region from the initial local volume of the second fluid in each region;
   generating a rise of a capillary ascension flow of the second fluid through the porous sample;
   during the rise of the capillary ascension flow, simultaneously measuring, in each region of the plurality of regions, a local volume of the second fluid, at successive instants, advantageously until the local volume is substantially steady, and determining, for each region, a plot of saturation in the first fluid in each region as a function of time, from the local volume of the second fluid measured at successive instants;
   determining a measured residual saturation in the first fluid in each region from the plot of saturation in the first fluid in each region as a function of time;
   determining the relation curve between the initial saturation in the first fluid and the residual saturation in the first fluid based on the measured initial saturations and the measured residual saturations in each region.

2. The method according to claim 1, wherein the mechanical load is applied by centrifugating the porous sample around a rotation axis, a first end of the porous sample being oriented away from the rotation axis and a second end of the porous sample being oriented toward the rotation axis.

3. The method according to claim 1, wherein establishing the steady state profile in the porous sample comprises:
   injecting the first fluid in the porous sample, forming an entry flow;
   simultaneously collecting fluid from the porous sample, forming an exit flow; and
   maintaining the mechanical load until a rate of the exit flow becomes substantially zero.

4. The method according to claim 1, wherein the local volume of the second fluid, in each region of the plurality of regions, is measured through nuclear magnetic resonance imaging, or X-Ray tomography.

5. The method according claim 1, wherein generating a rise of a capillary ascension flow of the second fluid through the porous sample includes:
   submerging a first end of the porous sample in the second fluid, the first end being oriented downward with respect to gravity, and a second end being oriented upward;
   maintaining a constant level of the second fluid around the first end of the porous sample during a capillary ascension of the second fluid through the porous sample.

6. The method according to claim 5, wherein the constant level of the second fluid is maintained in a plane with a second fluid feeding assembly comprising an upper burette and a lower burette containing the second fluid, an upper surface of the second fluid in the lower burette extending in the plane and an outlet of the upper burette opening in the lower burette, in the plane or below the plane.

7. The method according to claim 6, comprising monitoring the position of an upper surface of the second fluid in the upper burette.

8. The method according to claim 1, wherein during the rise of the capillary ascension flow, the simultaneously measuring, in each region of the plurality of regions, the local volume of the second fluid, at successive instants is carried out without moving the porous sample.

9. The method according to claim 1, wherein, in each region of the plurality of regions, the initial saturation in the first fluid is determined as the saturation in the first fluid corresponding to the initial local volume, and the residual saturation is determined as the saturation in the first fluid corresponding to a crossing of the tangents to the curve on each side of a change of regime in the capillary ascension through the porous sample.

10. The method according to claim 1, wherein the first fluid is a gas and the second fluid is a liquid.

11. The method according to claim 1, wherein the porous sample is a formation sample, in particular a rock sample.

12. The method according to claim 1, wherein the porous sample is substantially cylindrical and has a central axis, each region of the plurality of regions being a transversal slice delimited by two parallel planes perpendicular to the central axis.

13. The method according claim 1, comprising establishing a further steady state profile of a saturation in the first fluid in the porous sample with a different value of the mechanical load, generating a further rise of a capillary ascension flow and during the rise of the capillary ascension flow, simultaneously measuring, in each region of the plurality of regions, a new local volume of the second fluid, at successive instants, until the new local volume is substantially steady, and determining, for each region, a new plot of saturation in the first fluid in each region as a function of time, from the new local volume of the second fluid measured at successive instants;
- determining an additional measured residual saturation in the first fluid in each region from the new plot of saturation in the first fluid in each region as a function of time;
- determining the relation curve between the initial saturation in the first fluid and the residual saturation in the first fluid based on the measured initial saturations and the measured residual saturations in each region.

* * * * *